United States Patent
Paterson et al.

(10) Patent No.: US 6,921,719 B2
(45) Date of Patent: Jul. 26, 2005

(54) METHOD OF PREPARING WHOLE SEMICONDUCTOR WAFER FOR ANALYSIS

(75) Inventors: Allan Paterson, Austin, TX (US); David G. Halley, Los Osos, CA (US)

(73) Assignee: Strasbaugh, A California Corporation, San Luis Obispo, CA (US)

( * ) Notice: Subject to any disclaimer, the term of this patent is extended or adjusted under 35 U.S.C. 154(b) by 0 days.

(21) Appl. No.: 10/065,589

(22) Filed: Oct. 31, 2002

(65) Prior Publication Data

US 2004/0087146 A1 May 6, 2004

(51) Int. Cl.$^7$ ............................................. H01L 21/302
(52) U.S. Cl. ............................ 438/704; 438/7; 438/10; 438/16; 438/17; 438/692; 438/712
(58) Field of Search .................... 216/53, 57, 88; 438/7, 10, 16, 17, 692, 704, 712

(56) References Cited

U.S. PATENT DOCUMENTS

| | | | | |
|---|---|---|---|---|
| 6,395,580 B1 | * | 5/2002 | Tseng | 438/108 |
| 6,420,266 B1 | * | 7/2002 | Smith et al. | 438/692 |
| 6,441,475 B2 | * | 8/2002 | Zandman et al. | 257/685 |
| 6,448,801 B2 | * | 9/2002 | Dischiano | 324/765 |
| 6,630,369 B2 | * | 10/2003 | Rubin | 438/116 |
| 6,672,947 B2 | * | 1/2004 | Tsao et al. | 451/57 |
| 2002/0127821 A1 | * | 9/2002 | Ohya et al. | 438/459 |

FOREIGN PATENT DOCUMENTS

| | | | |
|---|---|---|---|
| EP | 999250 | * | 5/2000 |
| JP | 10-092776 | * | 4/1998 |
| JP | 2002-203828 | * | 7/2002 |
| JP | 2002-270560 | * | 9/2002 |

* cited by examiner

*Primary Examiner*—George A. Goudreau
(74) *Attorney, Agent, or Firm*—Thomas F. Lebens; Sinsheimer, Schiebelhut & Daggett

(57) ABSTRACT

A method for preparing a semiconductor wafer for whole wafer backside inspection is disclosed. The frontside of the wafer is covered with a protective frontside substrate and the backside portion of the wafer is thinned using conventional techniques. The whole wafer backside is then polished and a backside substrate, preferably of transparent material is juxtaposed to the backside of the wafer, such as with an adhesive or with a frame. The frontside substrate is then removed, exposing electronic devices for device inspection. The backside of the wafer is maintained open or available to backside inspection such as emission microscopy techniques used to detect defects which emit light.

24 Claims, 6 Drawing Sheets

METHOD OF PREPARING WHOLE SEMICONDUCTOR WAFER FOR ANALYSIS

BACKGROUND

1. Field of the Invention

The present invention pertains to the preparation of semiconductor wafers and in particular to the preparation of wafers for whole (or full) wafer backside analysis.

2. Description of the Related Art

The use of the semiconductor devices in today's commercial goods is undergoing dramatic growth. In order to expand the use of semiconductor devices in lower cost traditional products, semiconductor devices must be produced at previously unattainable low cost. Virtually every step of semiconductor device production is undergoing extensive investigation in an effort to obtain cost savings which will expand the market for semiconductor products. Lowering the cost of semiconductor devices will also enable further progress in state of the art technologies.

It is generally recognized that substantial cost savings can be employed if large scale manufacturing techniques can be brought to bear on whole wafers containing multiple, usually identical, electronic devices that are simultaneously formed on the wafer substrate, prior to the wafer being divided into individual units or dies. It has been found efficient in constructing semiconductor wafers that a substrate of semiconductor material, preferably silicon, receives overlying layers of active devices and inter-layer interconnects. After each layer is formed on the substrate, the frontside surface or active surface of the wafer is planarized or flattened so that succeeding layers are formed with a desired registry and upright orientation. Exceedingly stringent flatness requirements are necessary for small dimensioned patterning. As the layers are built up, one upon the other, a variety of electronic devices are formed on the wafer substrate and typically multiple, identical devices are simultaneously formed in the layer-by-layer operations. Usually, only the active surface or frontside surface of the wafer undergoes extensive flattening, with the reverse or backside remaining free of layering processes and the need for flattening steps. As will be appreciated, the techniques used for layer fabrication and the flattening processes cause stress inducing forces to be stored within the wafer construction. Gross chemical and atomic-level forces are also imparted to the internal structure of the semiconductor wafer and contribute to its loss of mechanical ruggedness.

Following wafer fabrication, the wafer undergoes testing in which individual electronic devices carried on the wafer are electrically tested for proper circuit performance and desired electrical characteristics. In one type of analysis, commonly referred to as a wafer electrical probe or a wafer sort, the wafer is mounted on a vacuum chuck and is indexed to bring different circuit devices into contact with electrical probes connecting the wafer device to external test circuitry. Such wafer electrical probes are typically performed on the frontside surface or active surface side of the wafer with the reverse or backside surface of the wafer lying outside of the area of interest.

With increasing development of semiconductor technology, different types of analyses are being developed. One area of investigation seeks to exploit advantages that can be obtained from reducing the overall thickness of the wafer, by removing inactive material from the backside surface of the wafer. While wafer thinning and aforementioned testing and analysis steps are carried out in individual semiconductor devices ("dies") formed by dividing the wafer, it is anticipated that substantial cost advantages (due to increased throughput; and relatedly an increased ability to quickly detect, and therefore remedy, process problems, so as to minimize the effect of such process problems, i.e., to minimize the number of wafers that are processed before such process problems are detected) can be obtained if such operations could be carried out on the multiple devices comprising a whole (or entire) semiconductor wafer, before the wafer is divided into individual die. Investigation of whole wafer manufacturing techniques has been seriously curtailed due to practical constraints associated with wafer strength. Due to relatively large wafer sizes and the trend to employ even larger size wafers, it is increasingly important that the wafer be mechanically strong to support its own weight and to withstand the rigors of post fabrication treatments, without cracking or other gross mechanical damage.

SUMMARY OF INVENTION

As mentioned, wafer analyses are typically carried out from the front or active surface of the wafer using electrical probes or other analytical techniques. There is however increasing interest in exploring the effectiveness of evaluation techniques carried out on the reverse or backside of the wafer surface. Such techniques have been less popular since the backside of the wafer includes a relatively thick substrate of circuit-inactive material, which causes, e.g., scattering of optical emissions from the electronic circuits at the active surface of the wafer. It is an object of some embodiments of the present invention to reduce wafer backside thickness, promoting the effectiveness of wafer backside analysis such as failure analysis by inspection of a wafer backside, using techniques such as emission microscopy or focused ion beam drilling, plus scanning electron microscope analysis to reveal structural details or faults.

In order to continue the advance of semiconductor analytical techniques, ongoing investigation has been carried out on individual semiconductor dies obtained by dividing a whole semiconductor wafer into units commonly referred to as "dies" or multiple dies referred to as "bars". Various techniques have been employed for such individual backside thinning, including ion beam etching as disclosed in U.S. Pat. Nos. 5,698,474 and 6,281,025. Chemical mechanical polishing or CMP techniques have also been used as described in U.S. Pat. No. 5,162,251, and oxidation techniques for wafer thinning are described in U.S. Pat. No. 4,615,762. It is an object of some embodiments of the present invention to provide practical whole wafer backside thinning using less costly techniques than are carried out according to any of the variety of techniques known today. A further object of some embodiments of the present invention is to provide a technique of whole wafer backside thinning using grinding and/or polishing techniques such as those employing full pad fixed abrasive sheets or full pad grinding wheels.

It is an object of some embodiments of the present invention therefore to provide whole wafer thinning techniques in which the whole wafer is prepared in a gross, universal or overall fashion. A related object of some embodiments of the present invention is to provide such techniques such that the various components or dies of the semiconductor wafer can be analyzed utilizing the same equipment and techniques, with a uniformity throughout the wafer leading to increased speed and reduced cost of wafer analysis.

A further object of some embodiments of the present invention is to provide whole wafer backside thinning techniques, which leaves all of die on the front of the wafer accessible for frontside inspection metrology.

Another object of some embodiments of the present invention is to provide wafer backside thinning techniques, which allow for automated whole wafer frontside and backside inspection.

Yet another object of some embodiments of the present invention is to provide methods of whole wafer backside thinning, which avoid compromising the strength or robustness of the wafer while leaving all of the active or circuit-essential components on the front of the wafer intact, and while leaving the backside of the wafer available for inspection.

DETAILED DESCRIPTION

Figure 1:
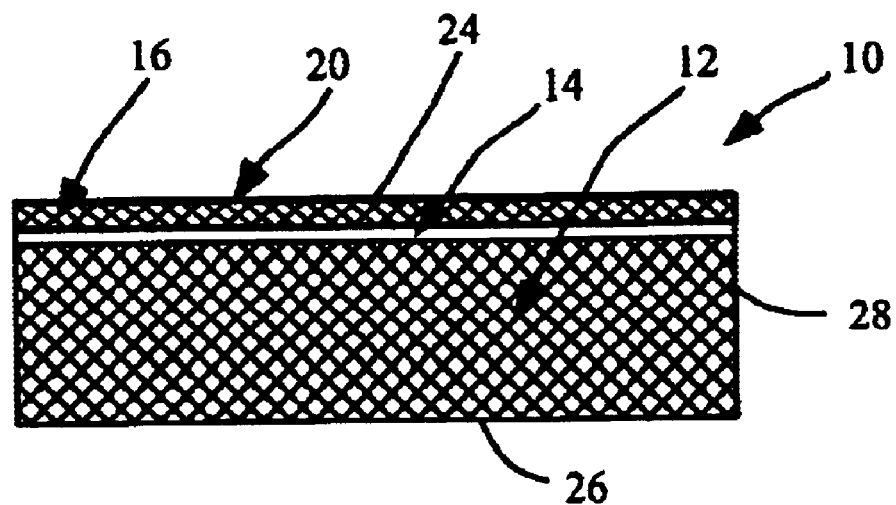
FIG. 1 is a cross-sectional view taken along the line 1—1 of FIG. 8.

The present invention, in some embodiments, is directed to the thinning of whole wafers in a way which prepares the wafer for whole wafer backside failure analysis without compromising the ability to carry out whole wafer failure analysis on the frontside of the wafer, as well. Utilizing the method of the present embodiments automated failure analysis can be carried out simultaneously on all semiconductor die portions. The present embodiments are compatible with different types of failure analyses known today to reverse engineer the design of other semiconductor devices, to increase the manufacturing yield by early identification of device faults, to improve quality and performance of the electronic devices, for product design and development, and to understand failure mechanisms by destructive examination of failed and unfailed electronic devices carried on the wafer, as well as reducing manufacturing costs by avoiding adding further value and cost to an individual defective electronic device, for example.

While different types of failure analyses are made possible by the present embodiments, the present embodiments find immediate application in the failure analysis of defects which emit light when powered. These faint light emissions from these types of defects, estimated to comprise at least 70% of all chip-level defects, can be optically observed (in the IR band and the visual band) by sensitive microscopes using powerful CCD detectors commonly employed with IR thermal-emission microscopy techniques. Faint light emissions related to chip-level defects can also be observed using scanning electron microscope (SEM) techniques.

Problems with traditional frontside inspection are increased with more complicated electronics, those involving a great number of interconnect layers. Utilizing principles of the present embodiments the backside surface layer of the whole wafer is thinned and supported for heretofore unattainable reliability and ruggedness needed for inspection and other post fabrication wafer operations. Prior to the present embodiments even if the semiconductor wafers could be thinned to the required dimensions, the whole wafers would be physically weakened, to the point where breakage of the whole wafer is likely to occur before desired post fabrication techniques can be completed. Certain failure analysis and other inspection techniques have not been available for many important doped silicon wafers. Commercially significant levels of silicon doping have been observed to absorb incident light to a point where the desired analytical techniques could not be successfully employed. With the present embodiments, backside wafer thinning allows infrared microscope inspections to detect important conditions including hot carrier emission detection and imaging, hot-spot detection, and thermal mapping. In one example according to principles of the present embodiments semiconductor wafers having, e.g., a "normal" thickness ranging between 600 and 900 microns are significantly reduced to a thickness of, e.g., approximately 200 microns or less, with the added advantage that the whole wafer, even though backside thinned to an unusual extent, is maintained in a physically robust condition with the whole wafer being reliably supported for subsequent handling and post fabrication techniques. Advantageously, backside inspection can be performed on, e.g., hundreds of uncut die making up a whole wafer simultaneously, instead of requiring a separate inspection for each die, as has been heretofore required. At the same time, by inspecting a whole wafer thinned to an unusual extent, much greater analysis accuracy can be achieved than with thicker whole wafers, because of the uncertainly introduced as a result of scattering caused by greater amounts of doped silicon (in thicker whole wafers) standing between analysis equipment and the electronic circuits generating optical emissions in response to electrical test stimuli. This is important in part because as circuit density increases in integrated circuits, greater accuracy is required to analyze the circuits. As a result, with the present embodiments, not only is the quantity of analysis increased, i.e., greater throughput, but the quality of the such analysis is maintained at a higher level than has been heretofore possible in whole wafer analysis. Further, substantially the entire frontside and backside portions of the whole wafer can be maintained open or available (optically, and, in some embodiments, mechanically) for simultaneous operations on virtually all of the components or die portions contained in the whole wafer.

Failure analysis of semiconductor wafers has been carried out despite the aforementioned weakening of the whole wafer when thinned to a significant extent. However, in order to carry out technical advances in the field of failure analysis, the wafer must be divided into its individual components, known as single chips or dies as a practical measure. Typically, a commercially significant whole wafer carries a large number of individual die portions, making it difficult to identify particular die portions suspected of failure, or otherwise targeted for inspection. Weakening caused by substantial thinning is reduced but each die of the wafer to be individually prepared and set up for inspection and analysis. Preparation and mounting of individual die samples for inspection involves a substantial expenditure of time and labor. Processing of individual dies gives rise to variability of quality and thickness across the individual die samples prepared, usually by hand, for backside analysis and inspection. The use of highly-skilled labor for hand operations on die pieces gives rise to variability in the end product cost, due to fluctuating labor conditions.

Processing of dies of a whole wafer for inspection or other failure analyses using conventional techniques can be prohibitively expensive, and accordingly practical cost containment mandates that only the lowest number of dies be processed consistent with statistical reliability. Even if the number of die samples to be investigated is constrained to low numbers, individual processing of the die samples results in variances arising from testing procedures. Often times it is desirable to carry out analyses using larger amounts of data in production monitoring for example, where, due to low failure rates, a large statistically significant number of die must be inspected and data gathered to make yield improvements.

As mentioned above, whole wafer backside thinning carried out to an extent to be commercially significant has been found to greatly weaken the whole wafer structure. Mechanical failure of the whole wafer structure has been expressed herein in terms of whole wafer breakage. It should be pointed out that significant backside thinning of commercial wafers frequently renders the wafers unable to support their own weight, resulting in bowing or sagging under the force of gravity. Vacuum retention forces associated with conventional vacuum chucks often exceeds the level of gravitational forces and exerts an influence on the whole wafer imparting a substantial bow or warp from one process chuck or process tool to another. The cyclic or repetitive distortion of the whole wafer imparts a stress to the whole wafer structure which increases its susceptibility to breakage. For these and other reasons, it has been found commercially impractical to employ whole wafer techniques, especially techniques involving more fully automated equipment, which are typically designed for use with wafers having normal substrate thicknesses several times greater than that needed for practical, commercially significant backside inspection.

Because sample whole wafers having commercially significant backside thinning are difficult and expensive to prepare, utilization of more fully automated whole wafer equipment has been hampered, often to the point of foregoing whole wafer thinning, succumbing to current industry standards of full thickness wafers. With the present embodiments all of the die of a whole wafer are made visible and accessible in a robust, mechanically well supported structure. The present embodiments provide the access needed for inspection of all die on production wafers using conventional automated inspection tools. This enables economically viable methods to achieve higher die yield from an integrated circuit fabrication plant and greater profitability for the end product. In addition, because process problems can be detected more quickly using the present embodiments (due to higher throughput), such process problems can be more quickly remedied, thereby reducing the numbers of wafers processed before such process problems are detected and corrected. Further, the present embodiments provide such advantages without conventional compromises. For example, failure analysis has typically been carried out on individual die or chips, by removing layers from the front or device side of the wafer, one layer at a time, until the area of interest was exposed to inspection. Such destructive testing techniques are costly, and are not conducive to high yield production management and control. With the present embodiments the whole wafer is maintained in a mechanically or structurally robust condition despite significant backside thinning carried out to an extent which makes available for whole wafer application, various optical thermal and other inspection methods developed using individual die.

Figure 8:
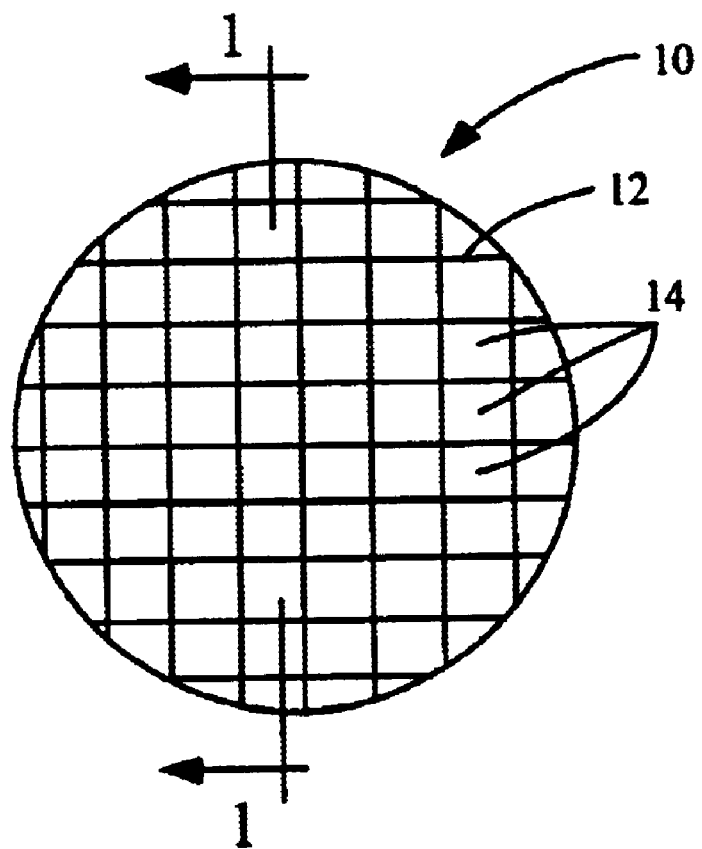
FIG. 8 is a top plan view of a semiconductor wafer with die components outlined by a reference grid.

Referring now to the drawings, and initially to FIG. 8, a semiconductor wafer generally indicated at 10 has a conventional circular shape when viewed in plan. A grid 12 of reference lines, indicate the outlines of die portions 14, typically (but not always) comprising identical electronic circuit devices. Wafer 10 may be constructed using virtually any known techniques, but often is constructed by building a series of layers, one on top of another, using a semiconductor substrate of silicon or other material. The layers built up on the substrate include a device layer as well as interconnect layers which electrically connect various portions of the active device layer to one another, as is known in the art.

Referring now to FIG. 1, the wafer 10 is shown in schematic cross-section. Included is the silicon wafer substrate 12. Active devices are schematically indicated at region 14 and interconnects are indicated in region 16. Regions 14 and 16 are indicated in highly simplified form, one region separate from another. In practice, practical electronic devices include many devices with portions of the active device layer electrically interconnected using interconnect structures. As will be appreciated by those skilled in the art FIG. 1 is further simplified in showing a region of interconnect 16 on top of a region of device structures 14. In many practical instances, the device and interconnect structures comprise complex three-dimensional shapes which occupy the interior regions of the fully fabricated semiconductor wafer. Bond pads providing electrical connection between the semiconductor wafer and external equipment are schematically indicated at 20. FIG. 1 depicts a full thickness or ordinary wafer construction. It is generally preferred that substrate 12 be as thin as practical and heretofore this has routinely resulted in minimal wafer substrate thicknesses as great as 600 to 750 microns. As will be seen herein, utilizing the given example, the wafer substrate thickness is reduced to approximately 200 microns or less, roughly one-third to one-fourth of these thicknesses.

Semiconductor wafer 10 is typically "built up" one layer at a time, although given layers can be applied in a locally non-uniform manner so as to create peaks or valleys when viewed in cross section (features which are not visible in the simplified version of FIG. 1). In order to preserve highly demanding registration of succeeding layers, and to provide optimal resolution of deposited structures, the semiconductor wafer is typically planarized or flattened as each succeeding layer is developed. Thus, wafer 10 is subjected to a substantial number of wafer handling operations as the wafer is moved back and forth between different tools. Throughout these operations, the electronic devices grow toward the frontside surface 24 while the backside surface 26 and peripheral edge 28 of the wafer remain undeveloped.

Figure 6:
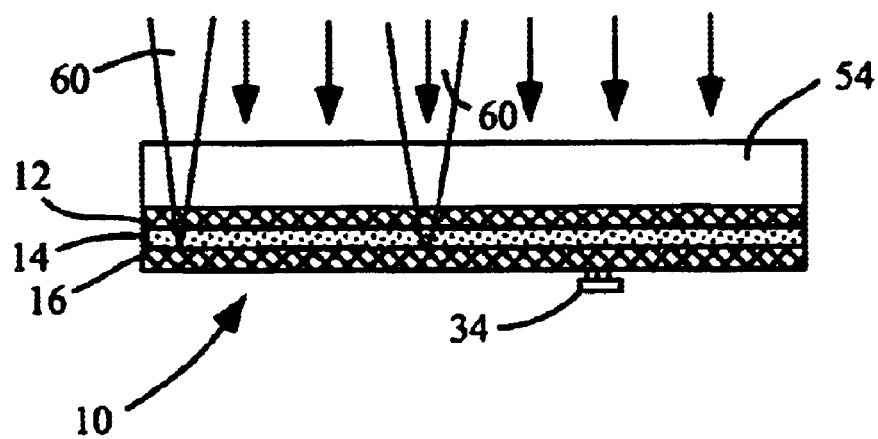
FIG. 6 is a cross-sectional view of a semiconductor wafer undergoing frontside and backside analysis.

As schematically indicated in FIG. 1, the frontside surface 24 contains bond pads 20 or other features for communication to external equipment. Typically, active inspections of the electronic devices carried in, i.e., comprising part of the whole wafer, are implemented by test probe equipment such as that schematically indicated at 34 in FIG. 6. Test signals are transmitted through the temporary interconnect 34 and operate to energize electronic circuits of the devices carried on the whole wafer. The temporary interconnect 34 illustrated in FIG. 6 is simplified, showing connection to one or more of a relatively low number of electronic devices. As will be seen herein, the present embodiments make the entire active surface of the wafer available for simultaneous whole wafer testing in which virtually all of (or a substantial fraction of) the electronic devices carried on the whole wafer are simultaneously electrically connected to external test equipment which can test the entire compliment of electronic devices either simultaneously or sequentially.

Figure 2:
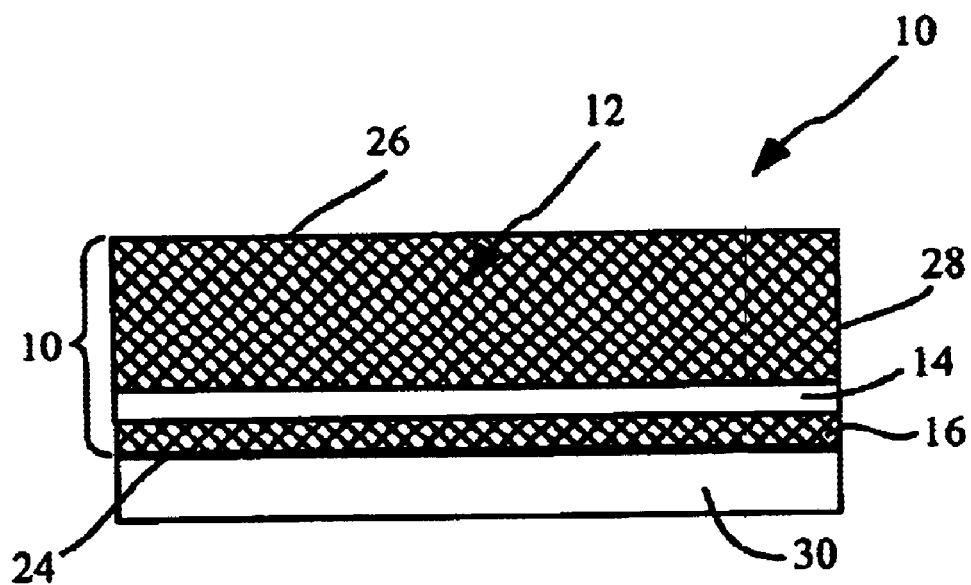
FIG. 2 is a cross-sectional view showing the semiconductor wafer of FIG. 1 bonded to a frontside substrate.
Figure 3:
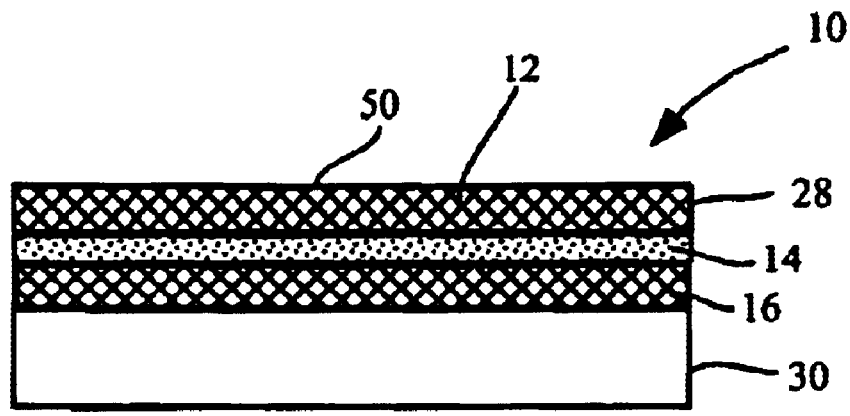
FIG. 3 is a cross-sectional view showing the wafer after backside thinning.

Referring to FIG. 2, a frontside substrate 30 is placed between the frontside surface 24 and the process chuck pr process tool (such as by applying the frontside substrate 30 to the frontside surface 24, sometimes referred to as the active side or active surface, of the wafer). It is important that frontside substrate 30 provide protection for the various wafer features needed for successful electronic operation of the devices carried by the wafer. For example, wafer frontside substrate 30 protects the electronic circuitry, interconnect, bond pads, bumps, ball grid arrays (BGA) or other connective features such as external connections on the front of the wafer, leaving these features intact and damage free throughout the remainder of method steps carried out, as will be described herein.

Referring again to FIG. 2, the frontside substrate 30 preferably covers the substantial entirety of the frontside surface of wafer 10, extending adjacent the peripheral edge 28 of the wafer. Frontside substrate 30, taken either alone or in combination with an external mounting device such as vacuum chuck, provides a rigid support for wafer 10. For example, frontside substrate 30 can comprise either rigid or non-rigid protective material of the type used with conventional vacuum chucks or similar supporting tools. Alternatively, frontside substrate 30 can comprise rigid or non-rigid vacuum-impermeable material. As will be seen herein, it is generally preferred that backside wafer thinning be carried out using grinding techniques using dedicated equipment such as in feed rotary surface grinders especially developed for semiconductor wafers. Such equipment typically employs sophisticated vacuum chucks. Accordingly, it is generally preferred that frontside substrate 30 be compatible with such equipment and to protect the frontside surface 24 of the finished wafer. As will be seen herein, it is generally preferred in carrying out the present embodiment that both frontside and backside surfaces of the wafer be available at the same time for examination and testing. Accordingly, it is preferred that frontside substrate 30 be readily removable from wafer frontside surface 24 when no longer required, without causing damage to the wafer frontside surface or requiring a substantial investment to remove frontside substrate 30 from wafer frontside surface 24.

With the frontside substrate installed, the semiconductor wafer is supported for backside thinning. As mentioned, the wafer substrate layer 12 is initially provided with the normal or conventional thickness need for self support of the wafer. As such, the wafer layer 12 is too thick for many desirable examination techniques to be performed for backside analysis of the whole wafer. Accordingly, the thickness of wafer layer 12 is reduced preferably using a conventional technique, such as, for example, ion-beam milling techniques such as those described in U.S. Pat. No. 5,786,236; backside reactive ion etches disclosed in U.S. Pat. No. 6,294,395; milling or ion beam etching techniques, such as those disclosed in U.S. Pat. Nos. 5,698,474 and 6,281,025; oxidation techniques, such as those described in U.S. Pat. No. 4,615,762; and/or chemical mechanical polishing (CMP) techniques such as those employed in U.S. Pat. No. 5,162,251.

Thinning is preferably carried out using grinding techniques such as those employing full pad fixed abrasive sheets or full pad grinding wheels (a round circle of abrasive material with embedded diamond abrasive, as opposed to a traditional cup wheel where abrasive is located only on the edge of the wheel). For example, wafer backside grinding is carried out using a fully automatic in-feed rotary surface grinder especially developed for semiconductor wafers, available from the Assignee of the present embodiment and commercially designated as a Strasbaugh 7AF grinder. Alternatively, and most preferably, grinding is married out utilizing a whole wafer surface finishing tool commercially available from the Assignee of the present invention designated bas a Strasbaugh 6EJ grinder/polisher. This last-mentioned tool is described in commonly assigned U.S. Pat. Nos. 6,227,956; 6,346,036; 6,361,647; 6,379,235; 6,450,860; 6,464,574; and U.S. patent application Ser. Nos. 09/693,148; 60/162,283; 09/699,286; 09/699,202; 09/699,290; 09/699,280; 09/699,285; 09/699,283; 09/699,287; 09/699,232; 09/706,349; 09/709,972; 60/299,337; 60/299,216; 60/299,400, tall of which patents and patent applications are incorporated herein as if fully set forth herein, in their entirety Accordingly, it is generally preferred that the thickness of wafer substrate 12 be reduced using precision surfacing processing machines such as the precision in-feed wafer grinder and whole wafer surface finishing tools mentioned above.

The whole wafer surface finishing tool mentioned above, commercially available from the Assignee of the present invention as a Strasbaugh 6EJ grinder/polisher provides additional advantages when combined with the method according to principles of the present embodiment. It has been discovered that wafer backside thinning is best carried out in a series of controlled stages including, for example, coarse grinding for bulk removal, medium grinding to remove worst grind lines, fine grinding to remove sub-surface micro-cracks, and polishing to provide a high quality surface finish. The Strasbaugh 6EJ grinder/polisher is especially adapted for multistage wafer backside thinning and is particularly suitable for carrying out method according to principles of the present embodiment since wafer backside thinning may be done while holding the wafer and related carrier on the same processing chuck.

Figure 4:
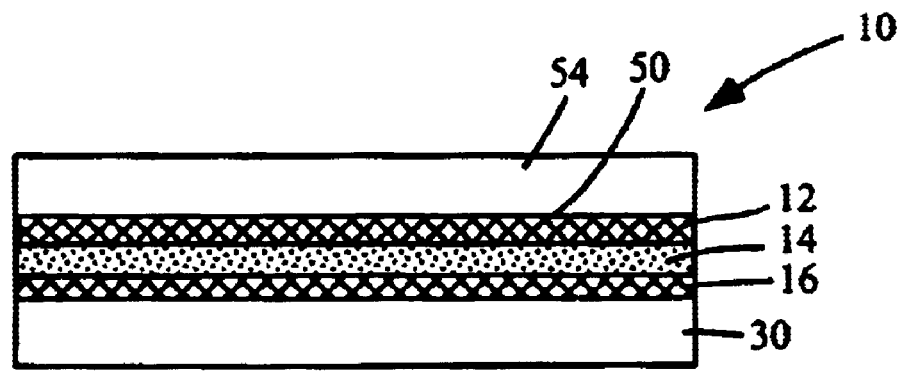
FIG. 4 is a cross-sectional view showing a semiconductor wafer with a backside substrate.

Depending upon the type of examination technique to be employed, final polishing may have to be carried out to critical specifications. For example, emission microscopy examinations require backside transparency to allow transmission of the desired wave lengths to examination equipment located at the backside of the prepared wafer. It is important that the thinned wafer backside surface be polished to prevent dispersion of visible energy within the wafer. As will be seen herein, a backside substrate is applied to the wafer backside surface, in one embodiment, after preparation. Alternative, an edge frame holder may be used to hold the wafer after preparation. It is important that the method of attachment maintain a continuous substantially transparent path from the active device site to the emission microscopy equipment located outside the wafer, adjacent its backside surface. The polished surface of the thinned wafer substrate 12 is indicated at 50. Referring to FIG. 4, a backside substrate 54 is attached, in accordance with one embodiment, to the exposed surface 50 of wafer substrate 12. In one aspect, substrate 54 is added to the wafer device to provide enhanced mechanical and structural stability. The backside wafer substrate 54 may extend throughout the entire backside surface of the wafer. The material chosen for the backside substrate 54 can comprise virtually any material known today, and may be constructed according to U.S. Pat. No. 4,946,716 which employs fused borosilicate glass and silica, for example. It is generally preferred that the material be chosen provide sufficient rigidity to support the thinned semiconductor wafer.

Figure 9:
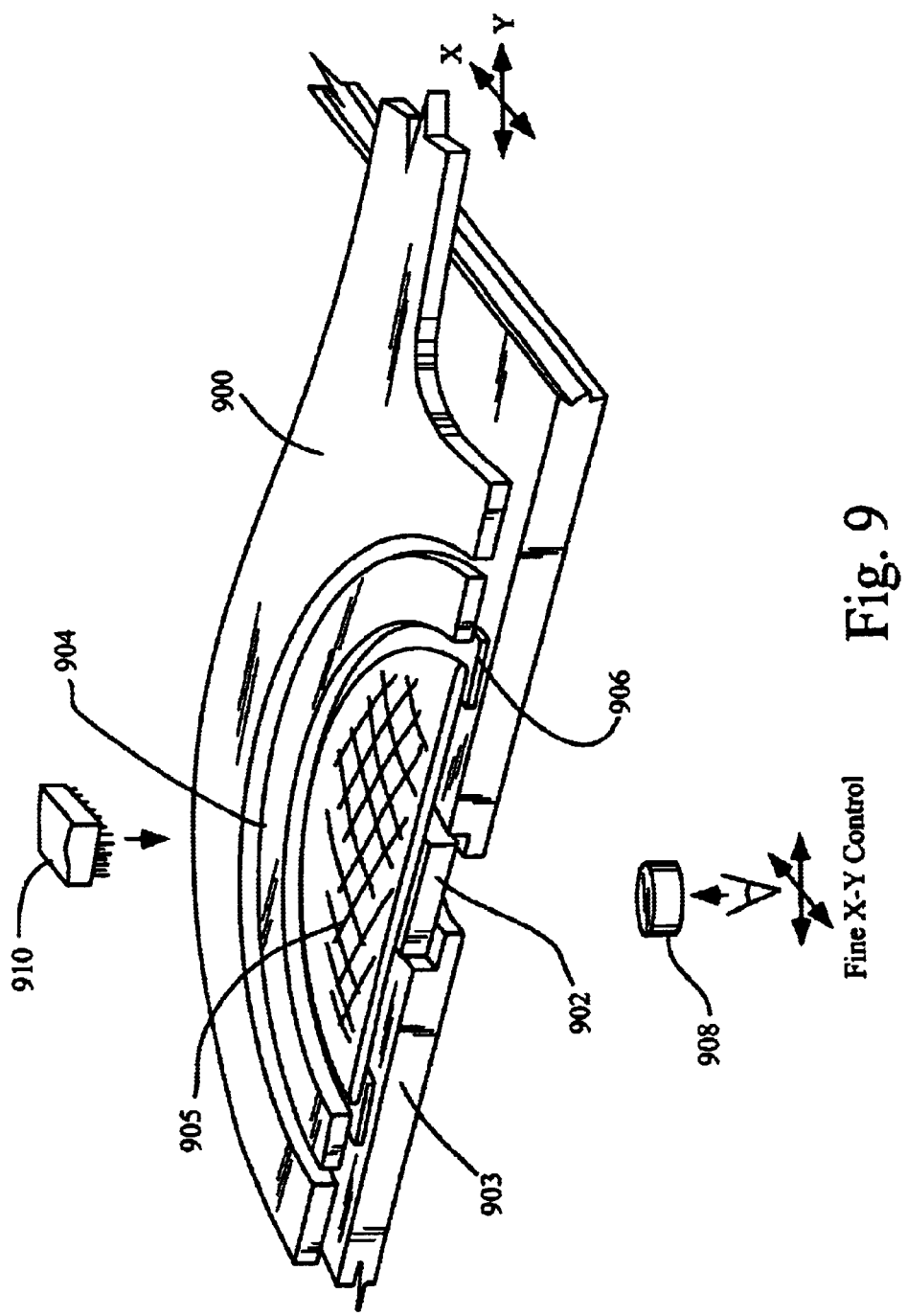
FIG. 9 is a perspective partial cross-sectional view of an edge-frame holder in accordance with one embodiment of the present invention.

As an alternative to the application of the backside substrate to the wafer, an edge frame holder, such as shown in FIG. 9 (and described in reference thereto) may be employed.

When used, the material for backside substrate 54 can be chosen without regard to light transmission when non-optical examination techniques are employed. However, if emission microscopy or other optical examination of thermal emissions is to be carried out, the material for backside substrate 54 should have a sufficiently, low impedance to the passage of light in the spectrum of interest. For example, FIG. 6 shows visible energy emanations 60 originating in the active device layer 14. Emanations 60 are associated with failure of electronic devices when energized by signals from outside equipment, with energy being transmitted to devices located within wafer 10 via temporary surface interconnect 34, as described above. In order to provide successful emission microscopy analysis in real time in a production environment, across whole wafer backside surfaces, it is important that the wafer substrate be thinned sufficiently and that the backside substrate and its joinder to the wafer substrate be sufficiently transparent to allow ready detection of the optical and/or thermal energy originating from device failures within wafer 10. If desired, the major opposed surfaces of backside substrate 54 may be coated with a conventional anti-reflective coating. The anti-reflective coating may be applied according to U.S. Pat. No. 6,107,107, for example, or virtually any conventional technique may be employed for the purpose.

Figure 5:
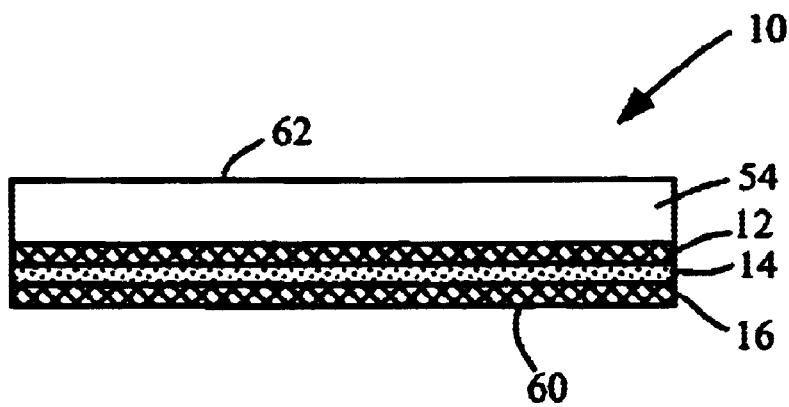
FIG. 5 is a cross-sectional view of a semiconductor wafer with the frontside substrate removed.

Once the backside substrate 54 is attached to the backside-thinned wafer the frontside wafer substrate 30 is detached and the frontside surface of the wafer is cleaned of any process material such as adhesive used to temporarily bond the frontside substrate to the semiconductor wafer. This leaves the structure illustrated in FIG. 5, comprising a semiconductor wafer having a frontside surface 60 and a backside surface 62 with the original semiconductor wafer components (schematically indicated at 12, 14 and 16) supported by a rigid backside substrate 54.

Figure 7:
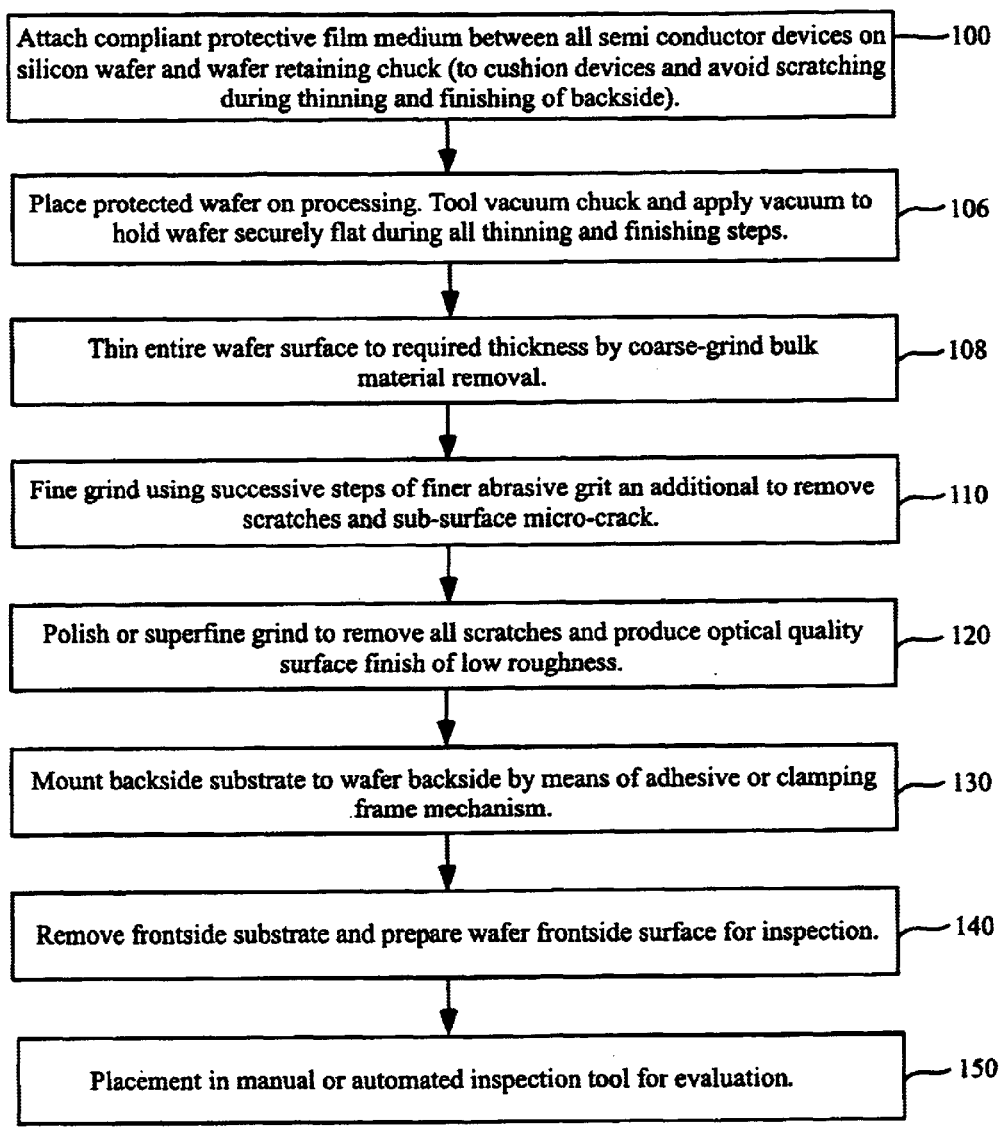
FIG. 7 is a schematic diagram illustrating method steps according to principles of some embodiments of the present invention.

Turning now to FIG. 7, a schematic block diagram illustrating the method according to principles of the present embodiment is shown. The first method step is performed on the frontside of a whole wafer to be processed. Typically, the whole wafer is one which has been fully fabricated and is ready for post fabrication finishing steps such as testing and examination. As will be recognized by those skilled in the art, the present embodiment can be carried out on virtually any type of whole wafer desired. The present embodiment provides non-destructive preparation for the whole wafer and can be employed for a number of purposes. As mentioned, the present embodiment has found immediate application in the field of whole wafer preparation for backside or frontside failure analysis. As has been pointed out above, the present embodiment provides heretofore unattainable unique advantages for backside wafer processing, especially whole wafer backside testing using any of a number of known examination techniques such as emission spectroscopy. As such, step 100 in the schematic diagram of FIG. 7 contemplates thinning of the wafer backside utilizing grinding and finishing techniques. In step 100, a whole wafer surface finishing tool having a wafer retaining chuck is provided. A frontside substrate is applied to the frontside surface of the wafer to protect electronic devices carried on the wafer at the frontside surface. As indicated in step 100, protection is provided to avoid scratching the frontside surface of the wafer during thinning and finishing of the wafer backside, in addition to cushioning the electronic devices located at the wafer frontside. As also indicated in step 100, it is generally preferred that the frontside substrate comprise a compliant film. In general terms, the compliant film is located between the frontside surface of the wafer and the wafer retaining chuck. However, in practice, it has been found convenient to attach the compliant film to the wafer frontside surface. Any of a variety of techniques can be employed. It is also possible although not required that the frontside surface of the wafer be mounted to a flexible carrier to allow bend stress testing.

In step 106 the protected wafer is placed on a vacuum chuck of the processing tool and vacuum is applied to hold the wafer securely flat during thinning and finishing steps carried out by the tool. Alternatively, wax mounting of the wafer onto the chuck may be used to hold the wafer securely flat during thinning and finishing steps. Several different tools known in the industry can be employed. Two examples of tools available from the Assignee of the present invention have been mentioned above. One tool, available from the Assignee of the present invention and sold as a Strasbaugh 6EJ grinder/polisher is preferred since the several stages of wafer backside thinning may be done while holding the wafer and related carrier on the same wafer retaining chuck.

Referring to step 108, the entire wafer backside surface is thinned to required thickness by coarse-grind bulk material removal. Preferably, thinning is accomplished using a back grinder with a peripheral wheel such as a super-abrasive wheel with 6 to 25 micron grit or a fixed abrasive pad with 9-micron grit available from Minnesota Mining and Manufacturing. Grinding is carried out to reduce the wafer from a full or ordinary thickness of approximately 700 microns to a destination thickness of approximately 200 microns. Abrasive materials referred to herein can be readily accommodated by the Strasbaugh 6EJ grinder/polisher which is most preferred for efficiency, economy and quality. Although other tools utilizing the same or different media can be employed to achieve the 200-micron destination thickness required.

Referring now to step 110, a fine grinding of the wafer backside surface is carried out to remove scratches and sub-surface micro-cracks. Preferably, fine grinding is carried out in a plurality of successive steps using grit ranging between 1 to 5 microns. Typically, an additional 20 microns of wafer thickness is removed in this step. Other finishing methods and tools are known in the art and can be employed as desired, although the Strasbaugh 6EJ grinder/polisher is preferred since the various steps required can be carried out on the same tool while holding the wafer and related carrier on the same processing chuck.

In step 120 the wafer is polished to remove all scratches and produce optical quality surface finish of low roughness on the wafer backside. Polishing is preferably carried out using cerium oxide with a small amount of silicon of 1 to 2 micron size. If desired, virtually any polishing technique can be employed, including so-called "super-fine grinding." The quality of the wafer backside surface finish carried out in step 120 is preferably adapted to the particular inspection techniques to be employed. As pointed out above, the present embodiment has found immediate application in the field of emission microscopy whole wafer inspection. Accordingly, it is important that step 120 be carried out to minimize or eliminate any optical "trapping" for reflecting of fault-generated energy within the wafer interior. Accordingly, the wafer backside surface is prepared in step 120 to optimize the transmission of fault-generated energy from the wafer to surrounding inspection devices. Other inspection techniques may have particular criteria which must be achieved in step 120, in a known manner.

Turning now to step 130, a backside substrate is mounted to the wafer backside using an inspection-appropriate adhesive or a mechanical arrangement such as a clamping frame mechanism. When the inspection method employs optical techniques such as emission microscopy, the inspection-appropriate adhesive is one which retains the desired light-transmission characteristics. In step 130 any necessary surface preparation of the exposed backside substrate surface is carried out in preparation for inspection. If optical examination techniques are to be employed, anti-reflective coatings may be applied to one or both major surfaces of the backside substrate.

Turning now to step 140, the frontside substrate is removed and the wafer frontside surface is prepared for inspection and/or application of voltage to the electronic circuits thereon. Preparation includes, for example, removing any adhesive or other substances used to attach the frontside substrate to the wafer frontside surface. If optical examination of the wafer frontside surface is to be carried out, an anti-reflective coating may be applied in step 140.

Turning now to step 150, the wafer is placed in the inspection tool for evaluation. The frontside of the wafer may be probed, and voltage applied to electronic circuits on the frontside, in order to elicit a measurable electrical, optical and/or thermal response from the electronic circuits on the wafer. Support at the backside of the wafer during probing (opposite the location of the probing on the frontside) can be provided entirely or in part by the backside substrate. Alternatively, such as when the clamping frame mechanism (edge frame holder) is employed, support can be provided by a backside support post placed opposite the location of the probing on the frontside. (Note that in accordance with a variation of the present embodiment employing a clamping frame mechanism, both optical and mechanical access to both the frontside and the backside of the wafer can be maintained.)

Existing automated whole wafer inspection methods and techniques used for thicker wafers, where a support window supports at the location opposite the location of the probing of the frontside.

As mentioned, substantial cost reduction can be attained with whole wafer inspection techniques. Further advantages are attained when whole wafer automated inspection is carried out. Inspection may involve infrared and/or visual emission microscopy for identifying defects on all die throughout the wafer. Thermal mapping and design evaluations can also be carried out according to principles of the present embodiment. It should be noted that both frontside and backside surfaces of the wafer can be inspected at the same time, if desired. With support and preparation of whole wafers according to principles of the present embodiment virtually any inspection technique known today can be carried out with improved efficiency and heretofore unattainable cost reductions in a commercial environment.

Referring next to FIG. 9, a perspective partial cross-sectional view of an edge-frame holder inspection apparatus is shown in accordance with one embodiment of the present invention.

Shown is an exiting wafer positioning stage 900, which is manipulated relative to an inspection window 902 by an X stepper motor (not shown) and a Y stepper motor (not shown) or other mechanical movement means. An aperture in the positioning stage 900 is coupled to an edge-frame holder 904, which is coupled via a ring of adhesive tape 906 to a peripheral edge of a thinned wafer 905. The inspection window 902 is held by a support frame 903, which is mechanically coupled to the X stepper motor and the X stepper motor, so as to allow the relative movement to be imparted between the wafer positioning stage. Below the aperture window 902 is a microscope system 908, which is fine adjusted in a plane parallel to the thinned wafer 905. This fine adjustment may be by, for example, high resolution positioning devices, i.e., an X positioning device (not shown) and a Y positioning device (not shown), e.g., microstepper or Piezo devices. A test probe 910 from above the thinned wafer 905, opposite the microscope system 908 is used to apply a voltage to devices at the frontside surface of the thinned wafer 905, which, in turn, elicits a photo-detectable thermal response from the electronic circuits at the frontside surface of the thinned wafer, which thermal response is observable through the backside surface of the thinned wafer 905 by the microscope system 908.

When the edge frame holder 904 is not employed, the backside substrate is used in order to mechanically support the thinned wafer 905 in the wafer positioning stage, and the edge frame holder 904 and the ring of adhesive tape 906 are not employed.

The drawings and the foregoing descriptions are not intended to represent the only forms of the invention in regard to the details of its construction and manner of operation. Changes in form and in the proportion of parts, as well as the substitution of equivalents, are contemplated as circumstances may suggest or render expedient; and although specific terms have been employed, they are intended in a generic and descriptive sense only and not for the purposes of limitation, the scope of the invention being delineated by the following claims.

What is claimed is:

1. A method of preparing a whole wafer of semiconductor material, having opposed front and back sides with respective surfaces and having at least one electronic device, comprising the steps of:

covering the frontside of the wafer with a whole wafer frontside substrate;

supporting the whole wafer with a whole wafer support coupled to the whole wafer frontside substrate, with the whole wafer frontside substrate protecting said at least one electronic device;

said whole wafer including a whole wafer substrate having an initial thickness and which includes said whole wafer backside;

thinning the whole wafer substrate, reducing its thickness to expose a new whole wafer backside surface at the backside of the whole wafer;

strengthening and rigidifying at least a portion of the new whole wafer backside surface to strengthen and rigidify at least a portion of the whole wafer; and removing the whole wafer frontside substrate, exposing said a least one electronic device while maintaining the strengthening and rigidifying of at least the portion of the new whole wafer backside surface to strengthen and rigidify at least the portion of the whole wafer.

2. The method of claim 1 wherein the strengthening and rigidifying at least the portion of the new whole wafer backside surface comprises:

providing a whole wafer backside substrate; and attaching the whole wafer backside substrate to at least the portion of the new whole wafer backside surface to strengthen and rigidify the whole wafer.

3. The method of claim 2 further comprising the step of polishing the backside of the whole wafer prior to attaching the whole wafer backside substrate.

4. The method of claim 1 further comprising the steps of providing an inspection carrier and attaching the inspection carrier to the wafer to support the wafer for access of inspection instruments to both the frontside and the backside of the whole wafer.

5. The method of claim 1 wherein the step of thinning the whole wafer substrate comprises grinding the whole wafer substrate to expose the new whole wafer backside surface.

6. The method of claim 5 wherein the step of thinning the whole wafer substrate comprises grinding the whole wafer substrate to expose the new whole wafer backside surface using full pad fixed abrasive grinding.

7. The method of claim 5 wherein the step of grinding the whole wafer substrate includes providing a backside grinder with a grind chuck and securing the whole wafer to the grind chuck.

8. The method according to claim 7 wherein the grind chuck includes a vacuum chuck for securing the wafer using vacuum forces.

9. The method of claim 2 wherein the whole wafer backside substrate is comprised of substantially transparent material and said step of attaching said whole wafer backside substrate to said whole wafer backside surface maintains the transparency of the whole wafer backside substrate so as to allow substantially transparent visual observation of said at least one electronic device from the backside of the wafer.

10. The method of claim 9 further comprising the step of performing failure analysis by inspecting the wafer backside utilizing emission microscopy to detect defects in said at least one electronic device which emits light.

11. The method of claim 2 wherein the step of attaching said backside substrate to said whole wafer backside surface comprises attaching said backside substrate with an adhesive.

12. The method of claim 2 wherein the step of attaching said backside substrate to said whole wafer backside surface comprises attaching said backside substrate with a substantially translucent adhesive.

13. The method of claim 2 wherein the step of attaching said backside substrate to said whole wafer backside surface comprises attaching said backside substrate with a substantially transparent adhesive.

14. The method of claim 13 wherein the adhesive is UV curable and said method further comprises the step of UV curing the adhesive.

15. The method of claim 2 wherein the step of attaching said backside substrate to said whole wafer backside surface comprises attaching said backside substrate with a substantially opaque adhesive.

16. The method of claim 1 wherein the step of supporting with said whole wafer support comprises engaging the edge of said whole wafer with an edge-frame holder to provide handling strength after backside thinning.

17. The method of claim 1 wherein said thinning step comprises etching the backside of said whole wafer wing focused ion-beam etching techniques.

18. The method of claim 1 wherein the step of covering the frontside of the wafer with a whole wafer frontside substrate comprises attaching the whole wafer frontside substrate to the frontside of the wafer with an adhesive.

19. The method of claim 18 further comprising the step of cleaning the frontside of the wafer after removing the whole wafer frontside substrate.

20. The method of claim 2 wherein the new whole wafer backside surface has a size and the whole wafer backside substrate is sized with a smaller size and the step of attaching comprises attaching the whole wafer backside substrate to a portion of said new whole wafer backside surface.

21. The method of claim 1 wherein said whole wafer frontside substrate is substantially rigid.

22. The method of claim 1 wherein said whole wafer frontside substrate is substantially flexible.

23. The method of claim 1 wherein said whole wafer frontside substrate is vacuum-porous.

24. A method of preparing a whole semiconductor wafer having opposed front and back sides with respective surfaces and having at least one electronic device, comprising the steps of:
    covering the frontside of the wafer wit a whole wafer frontside substrate;
    supporting the whole wafer frontside substrate in a vacuum chuck, with the whole wafer frontside substrate protecting said at least one electronic device;
    said whole wafer including a whole wafer substrate having an initial thickness and which includes said whole wafer backside;
    thinning the whole wafer substrate, reducing its thickness by grinding the wafer substrate to expose a ground surface at the backside of the whole wafer;
    polishing the backside of the whole wafer to provide a new whole wafer backside substrate surface;
    attaching the whole wafer backside substrate to the new whole wafer backside surface to strengthen and rigidify the whole wafer; and
    removing the whole water frontside substrate, exposing said at least one electronic device while maintaining the attachment of the whole wafer backside substrate to the whole wafer backside surface to strengthen and rigidify the whole wafer.

* * * * *

UNITED STATES PATENT AND TRADEMARK OFFICE
CERTIFICATE OF CORRECTION

PATENT NO. : 6,921,719 B2
DATED : July 26, 2005
INVENTOR(S) : Paterson et al.

It is certified that error appears in the above-identified patent and that said Letters Patent is hereby corrected as shown below:

Column 12,
Line 60, delete "a" and insert -- at --.

Column 14,
Line 8, delete "wing" and insert -- using --.
Line 32, delete "wit" and insert -- with --.
Line 48, delete "water" and insert -- wafer --.

Signed and Sealed this

First Day of November, 2005

JON W. DUDAS
*Director of the United States Patent and Trademark Office*